United States Patent [19]
Spears et al.

[11] Patent Number: 5,797,876
[45] Date of Patent: Aug. 25, 1998

[54] HIGH PRESSURE PERFUSION DEVICE

[75] Inventors: J. Richard Spears, Bloomfield Hills, Mich.; Philip S. Levin, Thompson, Conn.; Paul J. Zalesky, Huntington Beach, Calif.

[73] Assignees: Therox, Inc., Costa Mesa, Calif.; Wayne State University, Detroit, Mich.

[21] Appl. No.: 563,057

[22] Filed: Nov. 27, 1995

[51] Int. Cl.$^6$ ............................................. A61M 37/00
[52] U.S. Cl. ..................... 604/95; 604/264; 604/282; 604/280; 604/19
[58] Field of Search ........................ 604/49, 52, 53, 604/264, 27, 200, 95, 202, 19

[56] References Cited

U.S. PATENT DOCUMENTS

| | | | |
|---|---|---|---|
| 4,538,622 | 9/1985 | Samson et al. | 128/772 |
| 4,619,274 | 10/1986 | Morrison | 128/772 |
| 4,793,350 | 12/1988 | Mar et al. | 128/344 |
| 4,964,409 | 10/1990 | Tremulis | 128/657 |
| 5,211,636 | 5/1993 | Mische | 604/264 |
| 5,322,508 | 6/1994 | Viera | 604/52 |
| 5,498,251 | 3/1996 | Dalton | 604/282 |

OTHER PUBLICATIONS

Katzen™ Infusion Wires Product Description, Rev. 3/91

*Primary Examiner*—Wynn Wood Coggins
*Assistant Examiner*—N. Kent Gring
*Attorney, Agent, or Firm*—Pennie & Edmonds LLP

[57] ABSTRACT

The present invention includes a guidewire device capable of delivering perfusion fluids to a vascular site while at the same time exhibiting handling characteristics associated with existing non-perfusion guidewires. Preferred embodiments include a perfusion guidewire which closely matches the dimensions and physical characteristics of standard guidewires. Preferred embodiments also permit high pressure perfusion of supersaturated solutions, and include a liquid flow path which will not promote bubble generation or growth, or destabilize a supersaturated solution.

32 Claims, 9 Drawing Sheets

HIGH PRESSURE PERFUSION DEVICE

FIELD OF THE INVENTION

The present invention relates generally to medical devices for the delivery of fluids transluminally, more particularly to a perfusion device, and even more particularly to a high pressure perfusion guidewire.

BACKGROUND

Various medical procedures require fluids to be delivered to specific locations within the body, typically via a fluid delivery catheter. A narrow steerable guidewire is often used to maneuver through narrow, tortuous, and/or branching body passageways. After the guidewire has been directed to the desired location, a fluid delivery catheter may be inserted over the guidewire. The guidewire is usually removed before fluid delivery begins. Guidewires which are themselves capable of fluid delivery (such as that disclosed in U.S. Pat. No. 5,322,508) are also known in the art.

During balloon angioplasty procedures, a catheter equipped with a small balloon is inserted (usually over a guidewire) into an artery that has been narrowed, typically by the accumulation of fatty deposits. The balloon is then inflated to clear the blockage or lesion and widen the artery. Upon balloon inflation, blood flow distal to (i.e., "downstream" from) the inflated balloon may be almost completely stopped.

Myocardial ischemia (i.e., a reduction in blood perfusion to the heart muscle) occurs transiently in the majority of patients undergoing coronary angioplasty procedures, such as balloon angioplasty, directional atherectomy, rotational atherectomy, and stent deployment. The permissible duration of occlusion due to balloon inflation or other device deployment is normally determined by the severity of myocardial ischemia. Typically, evidence of severe ischemia (including patient chest pain and ECG changes) requires that the operator deflate the balloon or remove the occlusive device after approximately 60 to 120 seconds. For anatomically difficult lesions, such as type B and C lesions, longer periods of balloon inflation (or other device deployment) are frequently desirable for the first balloon inflation or other device deployment.

Autoperfusion balloon catheters, and catheters of the type disclosed in U.S. Pat. No. 5,322,508, can in some circumstances allow longer periods of balloon inflation. However, the blood (or other physiologic liquid) flow through such devices is frequently insufficient to provide an adequate oxygen supply to tissues distal to the angioplasty balloon or other occlusive device.

Recent advances in the generation and application of oxygen supersaturated solutions have made it possible to deliver greater amounts of oxygen to tissues distal to an angioplasty balloon. U.S. Pat. No. 5,407,426, and pending applications Ser. No. 08/273,652, filed Jul. 12, 1994, entitled "Method for Delivering a Gas-Supersaturated Fluid to a Gas-Depleted Site and Use Thereof"; Ser. No. 08/353,137, filed Dec. 9, 1994, entitled "Apparatus and Method of Delivery of Gas-Supersaturated Liquids"; Ser. No. 08/453, 660, filed May 30, 1995, entitled "Method for Delivering a Gas-Supersaturated fluid to a Gas-Depleted Site and Use Thereof"; Ser. No. 08/465,425, filed Jun. 5, 1995, entitled "Method for Delivery of Gas-Supersaturated Liquids"; Ser. No. 08/484,279, filed Jun. 7, 1995, entitled "Apparatus and Method of Delivery of Oxygen-Supersaturated Physiologic Solutions During Clinical Procedures"; and Ser. No. 08/484, 284, filed Jun. 7, 1995, entitled "High Pressure Gas Exchanger", which are incorporated herein by reference, disclose various methods for the generation and application of oxygen supersaturated liquids.

As is described in the above referenced patent applications, the generation, transport and delivery of oxygen supersaturated liquid may require the application of very high hydrostatic pressures. Accordingly, there remains a need for a high pressure fluid delivery device capable of infusing bubble-free fluid, which is supersaturated with oxygen, to vessels or ducts through and beyond the central lumen of a balloon angioplasty catheter or similarly occlusive device. There remains a further need for a quick connect/disconnect assembly which can withstand high pressures that may be experienced in delivering such oxygen supersaturated liquids from a fluid reservoir to a suitable fluid delivery device, and which can minimize the time required for the initiation or termination of oxygen supersaturated liquid perfusion.

SUMMARY

Accordingly, it is an object of the present invention to provide a guidewire device capable of delivering perfusion fluids to a vascular site while at the same time exhibiting handling characteristics associated with existing non-perfusion guidewires so that additional education or retraining of operators is reduced or eliminated.

Preferred embodiments of the present invention meet the foregoing needs by providing a perfusion guidewire which closely matches the dimensions and physical characteristics of standard guidewires in diameter, length, flexibility, column strength, torque transfer, surface friction, kink resistance, radiopacity (i.e., opacity to x-rays), non-thrombogenicity (i.e., tendency not to promote blood clots) and bio-compatibility. Preferred embodiments of the invention permit high pressure perfusion and also include a liquid flow path which will not promote bubble generation or growth, or destabilize the oxygen supersaturated solution.

A high pressure perfusion guidewire according to the invention preferably includes three sections: a tubular proximal segment or handle, which comprises the greater part of the perfusion guidewire length; a transitional region including a "quill-like" lip which provides the desired torque transfer and pressure drop characteristics; and a distal segment which conveys the fluid out of the perfusion guidewire, but also mimics the distal functions of a standard coronary guidewire.

The proximal segment may be connected to a fluid source using standard connectors known to those skilled in the art.

3

DETAILED DESCRIPTION

The structure and function of the preferred embodiments can best be understood by reference to the drawings. The reader will note that the same reference numerals appear in multiple figures. Where this is the case, the numerals refer to the same or corresponding structure in those figures.

The present invention includes several embodiments of a perfusion guidewire. As will be made clear below, the major differences between the various embodiments are in the transitional region and distal segments. Persons of ordinary skill in the art will understand that the alternative regions or segments may be used together in combinations other than described in detail below, based on the teachings contained herein.

Transluminal Fluid Delivery System

Figure 1:
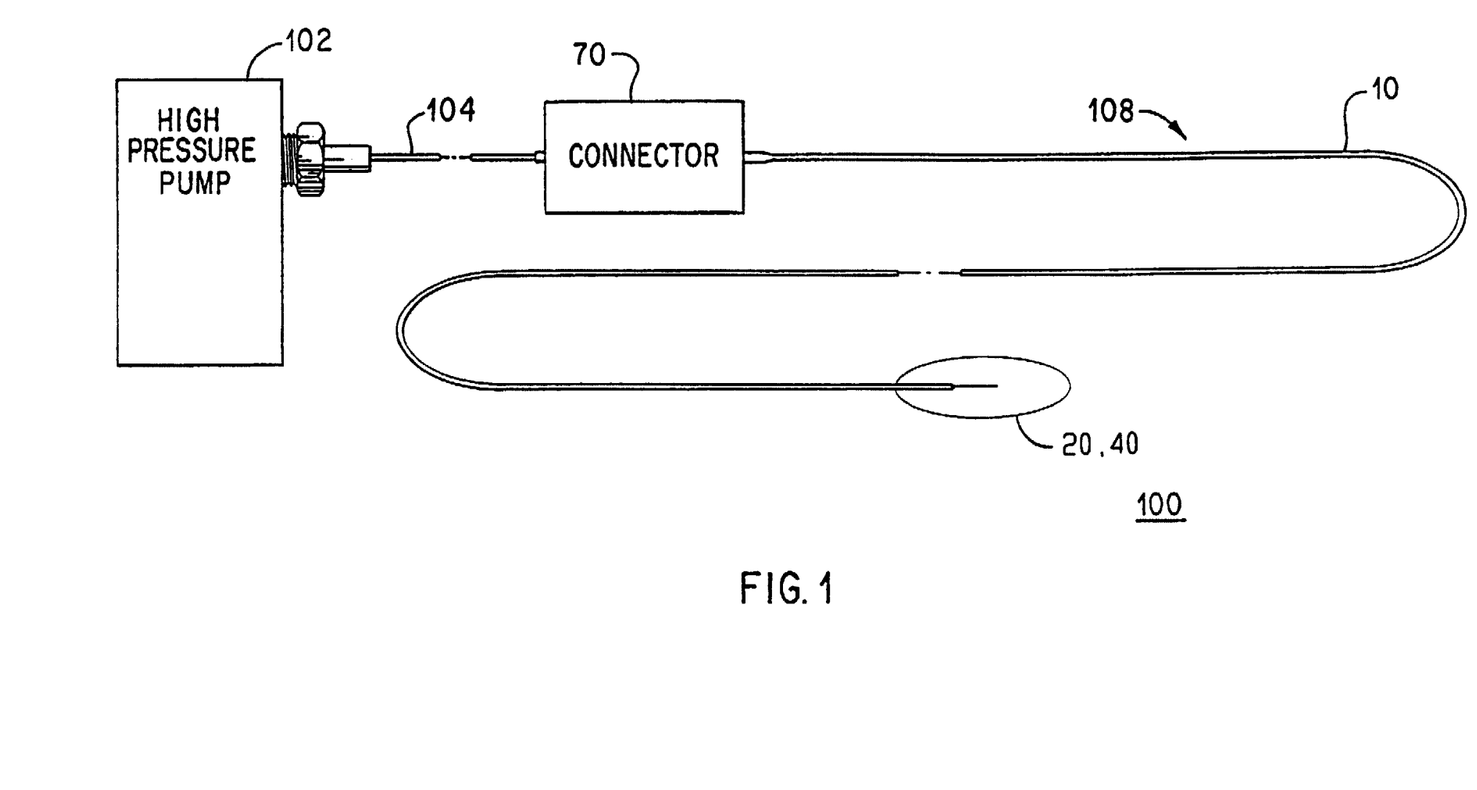
FIG. 1 shows a transluminal fluid delivery system including a high pressure perfusion device according to a preferred embodiment of the invention.

FIG. 1 shows a transluminal fluid delivery system 100 according to a preferred embodiment of the invention. Fluid delivery system 100 includes a high pressure source 102, such as a pump or reservoir, a connector 70, a tube 104 connecting an output of high pressure source 102 to an input of connector 70, and a perfusion guidewire 108. As will be discussed further below, each embodiment of perfusion guidewire 108 includes a handle or proximal segment 10, a transitional region 20, and a distal segment 40.

Proximal Segment or Handle

Figure 2:
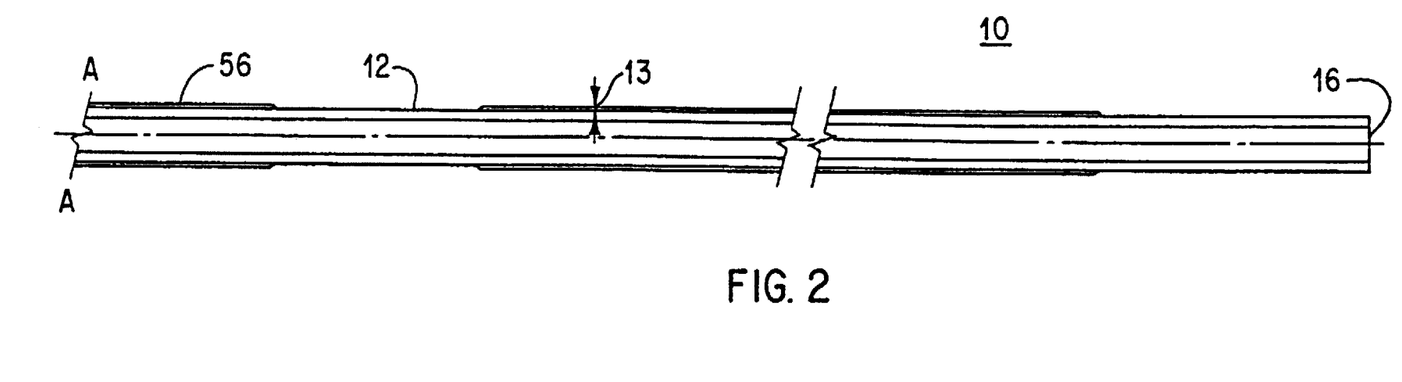
FIG. 2 is a cross sectional view of the proximal portion of a high pressure perfusion guidewire according to the invention.

Referring now to FIG. 2, a handle or proximal segment 10 of perfusion guidewire 108 is shown. Proximal segment 10 includes a thin-walled tube 12 which defines a lumen. Tube 12 is made of bio-compatible material, has the appropriate dimensions, and the appropriate burst strength, flexibility, torque transfer, and kink resistance characteristics for use as a perfusion guidewire as described herein. Tube 12 is preferably coated over most of its length with a low friction, thin film bio-compatible coating 13, such as PTFE. Tube 12 also has an opening 16 for connection to a source of high pressure, oxygen supersaturated liquid.

In one embodiment, tube 12 of proximal segment 10 is preferably a 304 stainless steel tube having a 0.0145" outside diameter, a 0.010" inside diameter, and a length of approximately 150 cm. Tube 12 preferably also has a 0.0004" to 0.0007" thick coating 13 of PTFE over its full length, except for a few cm at each end. In another embodiment, tube 12 of proximal segment 10 is a 304 stainless steel tube having a 0.0132" outside diameter, a 0.008" inside diameter, and a length of approximately 150 cm. In this embodiment, tube 12 would also preferably have a 0.0004" to 0.0007" thick coating of PTFE over its full length, except for a few cm at each end. If necessary to avoid kinking during the initial part of a procedure, a support wire or stylet (not shown) may be inserted in tube 12. The support wire or stylet would be withdrawn before liquid is introduced into tube 12.

Transitional Region

Figure 3:
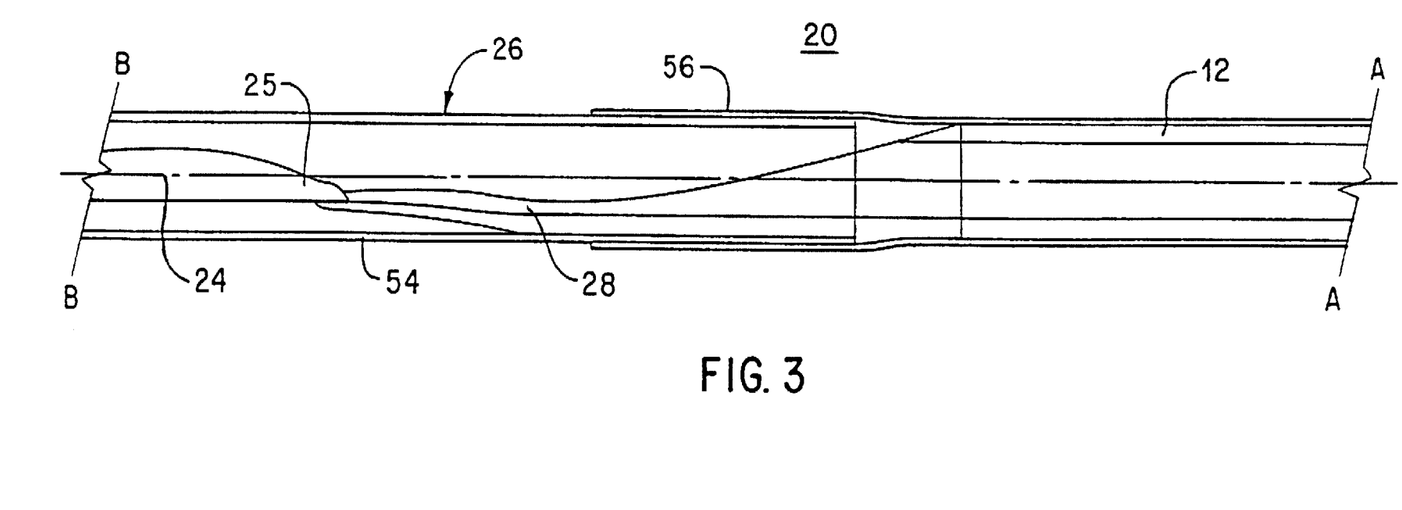
FIG. 3 is a cross sectional view of the transitional region of a high pressure perfusion guidewire according to the invention, continued from FIG. 2.

Referring now to FIG. 3, one embodiment of a transitional region 20 of perfusion guidewire 108 is shown. Transitional region 20 provides a transition between tube 12 and the region defined by core wire 24 and sheath 26. The transitional region 20 also is designed to achieve the objective of providing a perfusion guidewire with the handling characteristics of a "standard" guidewire. "Standard" guidewire is used herein to refer to the typical non-perfusion guidewires commonly used today for various procedures. Such procedures may involve coronary or peripheral vessels. Examples of guidewires considered to be standard guidewires are shown in U.S. Pat. Nos. 4,538,622 and 4,619,274. Based on the teachings contained herein, a person of ordinary skill in the art may select the various parameters of the present invention to achieve handling characteristics substantially the same as those of the above guidewires, or any other handling characteristics desired for a particular procedure.

In one embodiment, the distal end of tube 12 is ground or otherwise machined eccentrically so that a tapered lip 28 is created which resembles the nib end of a quill pen. Alternatively, a separate lip may be secured to the end of the tube. By way of example, for the tube 12 dimensions described above, lip 28 is preferably between 1 and 5 cm long, and is preferably tapered smoothly to a final dimension of 0.006" wide and 0.001" thick. This "quill-like" lip 28 provides several advantages.

First, lip 28 provides a low resistance transition, since the transition from tube 12 to the region defined by core wire 24 and sheath 26 is accomplished with little or no decrease in cross-section flow area, and in some instances even net increase. Second, lip 28 provides a smooth flow transition because lip 28 is tapered; there are no abrupt changes in the flow path geometry. These first two characteristics reduce the possibility that cavitation or bubble formation will take place in a supersaturated solution flowing through the guidewire. As a third advantage, lip 28 provides a convenient and strong attachment point for the distal core wire 24. Finally, lip 28 provides a joint between core wire 24 and tube 12 which creates a smooth transition in terms of flexibility and stiffness. The taper of lip 28 may be easily adjusted to match any desired flexibility profile. In particular, the taper may be adjusted to match the flexibility profile of a standard coronary guidewire.

An important element of guidewire design involves the transfer of torque from the proximal end of the guidewire, where the physician manipulates the guidewire, to the distal end. A smooth, even rotary action is required of a guidewire, even in a tortuous vascular pathway. Because lip 28 is not axially symmetric, it can exhibit a "cast" or unevenness in rotary motion when it is passed over a sharp bend. To reduce the cast, lip 28 is preferably sufficiently short in length and core wire 24 is long enough such that lip 28 is positioned proximal of any sharp bends in the vascular pathway during use. In practice, it is usually sufficient to locate lip 28 proximal of the aortic arch during a coronary angioplasty procedure.

Figure 4:
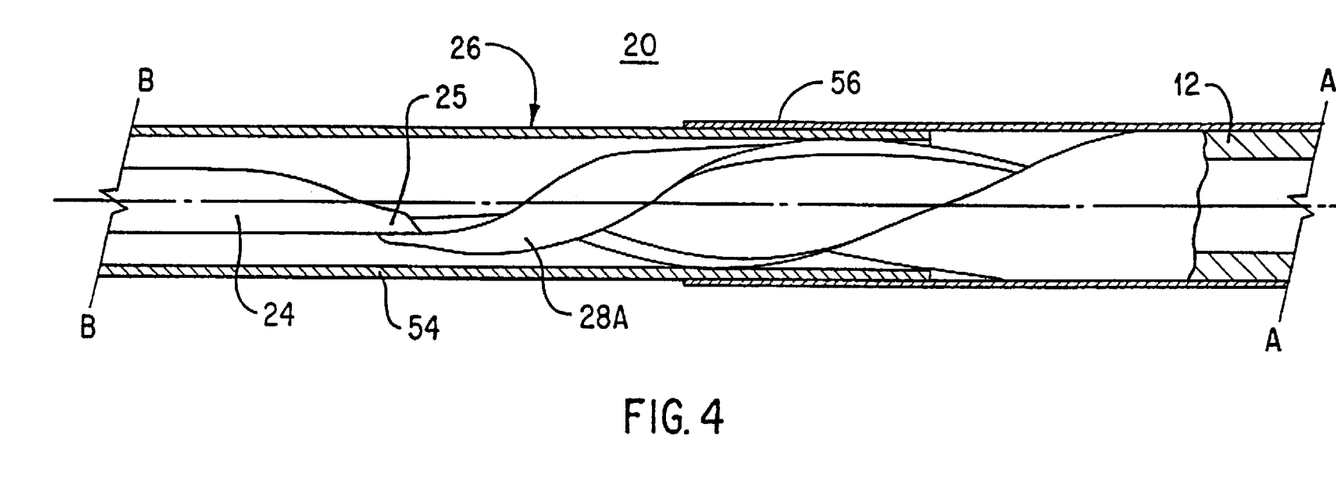
FIG. 4 is a cross sectional view of the transitional region of an alternative embodiment of a high pressure perfusion guidewire according to the invention, also continued from FIG. 2.

Referring now to FIG. 4, an alternative embodiment of transitional region 20 is shown. In procedures where transitional region 20 must encounter vascular tortuosity, or it is otherwise desirable to greatly reduce the cast, a lip 28A may be fashioned from the distal end of tube 12 into a helical form. Lip 28A will exhibit more evenness in rotary motion when passed over sharp bends than lip 28, but lip 28A will still maintain the aforementioned advantages of the non-helical lip 28. Exemplary dimensions for lip 28A with the tubes described above are 5 cm long, and tapered smoothly to a final dimension of 0.006" wide and 0.001" thick.

Distal Segment

Figure 5:
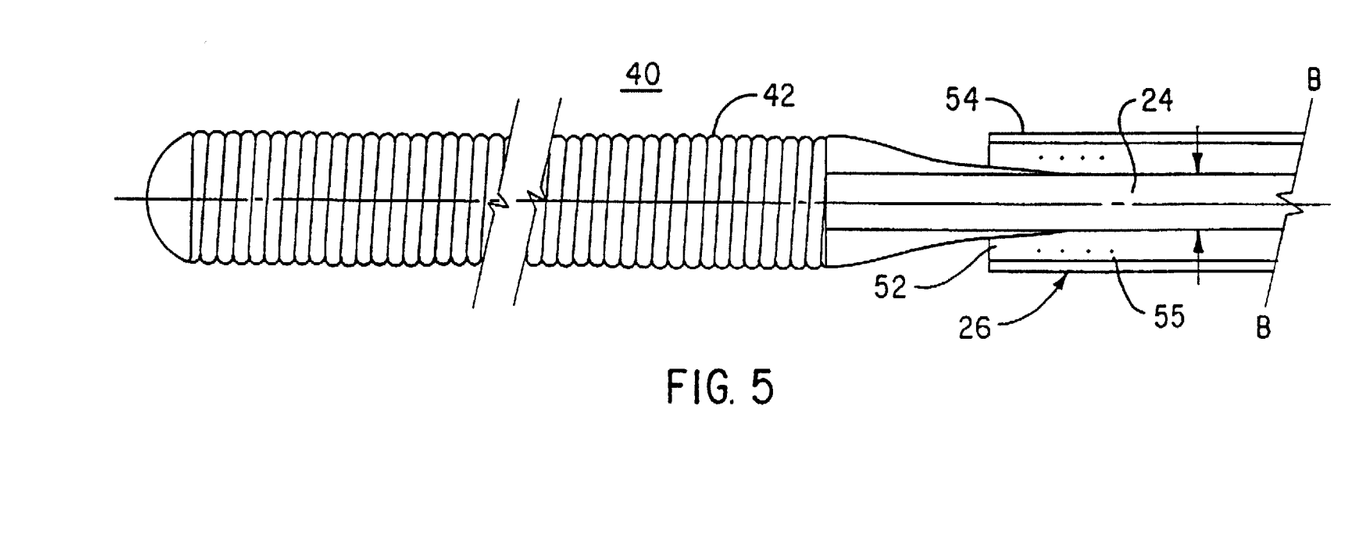
FIG. 5 is a partially cross sectional view of the distal segment of a high pressure coronary perfusion guidewire according to the invention, continued from either of FIGS. 3 or 4.

FIG. 5 shows one embodiment of a distal segment 40 of perfusion guidewire 108. Distal segment 40 includes core wire 24, thin-walled sheath 26 and a distal coil or coil spring 42. The material properties and dimensions of distal segment 40 are preferably selected to match the physical properties of standard coronary guidewires.

In an exemplary embodiment, sheath 26 comprises approximately 30 cm of high strength polymer tubing 54, having an outside diameter of about 0.0145" and an inside diameter of about 0.0135", and approximately 4 cm of polyester heat shrink tubing 56 in the transitional and proximal regions (See FIGS. 2–4) having an approximate, unrecovered inside diameter of 0.017" and a wall thickness of about 0.0005". Tubing 54 is preferably made of polyimide. At the proximal end of sheath 26, the polyimide tubing 54 is placed over lip 28 or 28A to within 1 cm of the proximal end of lip 28 or 28A. Polyester heat shrink tubing 56 forms a bridging joint between tube 12 and polyimide tubing 54. A thin epoxy film (not shown) is applied beneath heat shrink tubing 56, and then heat shrink tubing 56 is heat sealed to form a leak-free bond with tubing 12 and polyimide tubing 54.

In an alternative embodiment (shown, for example, as the proximal portion of FIG. 15), sheath 26 comprises approximately 35 cm of high strength polymer tubing 54, having an outside diameter of about 0.0145" and an inside diameter of about 0.0135". Tubing 54 is preferably made of polyimide. At the proximal end of sheath 26, the polyimide tubing 54 is placed over lip 28 or 28A and onto a portion of tube 12 proximal to lip 28 or 28A. A thin epoxy film (not shown) is applied beneath polyimide tubing 54 to form a leak-free bond with tubing 12.

The polyimide tubing 54 is preferably coated with a thin film of a lubricious hydrophilic coating. Appropriate hydrophilic coatings, such as BSI PV01/PVP, are well known to those skilled in the art.

At its distal end, polyimide tubing 54 of sheath 26 may be open- or close-ended. If polyimide tubing 54 is close-ended, it may be configured with a number of sideports 55 or some such means to allow flow to exit sheath 26. The sideports 55 can be made as a plurality of perforations which are typically between about 15–50 µm in diameter, arranged along about a 2 cm length. The open end 52 of polyimide tubing 54 may be positioned over distal coil 42, or it may terminate before coil 42 as is shown in FIG. 5. Alternatively, the distal end of polyimide tubing 54 may overlap distal coil 42 and be bonded with epoxy to distal coil 42 as shown, for example, in FIG. 15. Polyimide tubing 54 may also be attached to an exposed portion of core wire 24. If polyimide tubing 54 is open-ended, it may be terminated with a bevel or a square cut open end 52, and may also be configured with a number of sideports 55. The actual configuration of the openings and total area can be selected by a person of ordinary skill based on the teachings herein.

As was discussed above, core wire 24 is attached at its proximal end to the distal end of lip 28 or 28A (see FIGS. 3 and 4). At its distal end, core wire 24 is embedded at least partially into distal coil 42 as is known in guidewire construction. Core wire 24 may have any appropriate cross-sectional shape, length and diameter.

In an exemplary preferred embodiment, core wire 24 is approximately 35 cm long with a circular cross section. Over the proximal 24 cm, core wire 24 has an outside diameter of about 0.006". It then tapers smoothly over a approximately 2 cm distance to an outside diameter of about 0.005", and is constant at this diameter for approximately 5 cm. Core wire 24 then tapers down to an outside diameter of about 0.003", where it is embedded within distal coil 42. Core wire 24 is ground at the proximal end to form a 3 mm long entrance taper 25 which provides a smooth flow transition from lip 28 or 28A, as discussed above (See FIGS. 3 and 4). The entrance taper 25 is typically lap-joined with an appropriate solder (such as 96.5/3.5 tin/silver solder) to lip 28 or 28A, with an overlap of about 1.5 mm. Core wire 24 is preferably coated with a thin film of an appropriate hydrophilic coating.

Distal coil 42 serves as a compliant leading edge for the atraumatic and formable guidewire. The requirements, construction and dimensions of distal coil 42 are well known to those skilled in the art. In a preferred embodiment, distal coil 42 is 4 cm long with an outside diameter of 0.010" to 0.014". Distal coil 42 is preferably coated with a thin film of an appropriate hydrophilic coating such as BSI PV01/PVP. Distal coil 42 is also preferably radiopaque along its distal 2 cm, and may have a bend or cast at its distal end to allow the physician to "steer" the guidewire along tortuous passageways.

The disclosed perfusion guidewire is preferably inserted and used in the same manner as a standard coronary guidewire using a conventional torquing handle (not shown). As is known to those skilled in the art, a torquing handle is a hollow tube with an annular screw-down clamp similar to the chuck of a drill. It is slipped over the proximal end of the guidewire and screwed down to securely hold the guidewire to allow its manipulation. The preferred embodiments of the invention exhibit substantially the same performance characteristics as a standard guidewire, and can be inserted and used with conventional instrumentation and techniques. For this reason, a perfusion guidewire according to the invention could be regularly substituted for a standard guidewire, so that in the event a perfusion need arises during a procedure, there is no need to exchange guidewires. In a typical procedure using the present invention, the perfusion guidewire is inserted into the patient's vasculature and advanced to the treatment site using known techniques. This might involve crossing a lesion for application of balloon angioplasty. However, unlike standard guidewires, when the vessel is occluded during a procedure, flow in the vessel can be maintained by perfusing fluid through the guidewire of the present invention.

Other Alternative Embodiments

As was discussed above, the present invention includes several embodiments of perfusion guidewire 108. Several alternative embodiments of transitional region 20 and distal segment 40 will be discussed below. Also, dimensions provided herein are preferred dimensions for a particular size of device as described. Persons of ordinary skill in the art may appropriately size a device by modifying the preferred dimensions without departing from the scope of the invention.

Transitional Region

Figure 6:
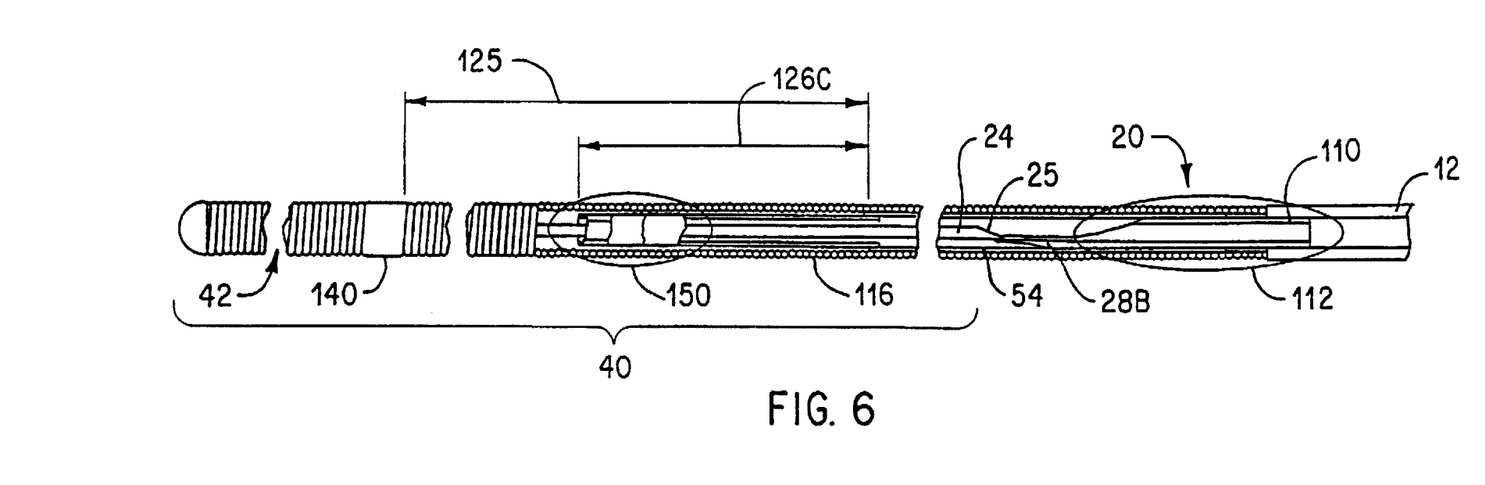
FIG. 6 is a partial cross sectional view of the transitional region and distal segment of an alternative perfusion guidewire according to the invention.
Figure 8:
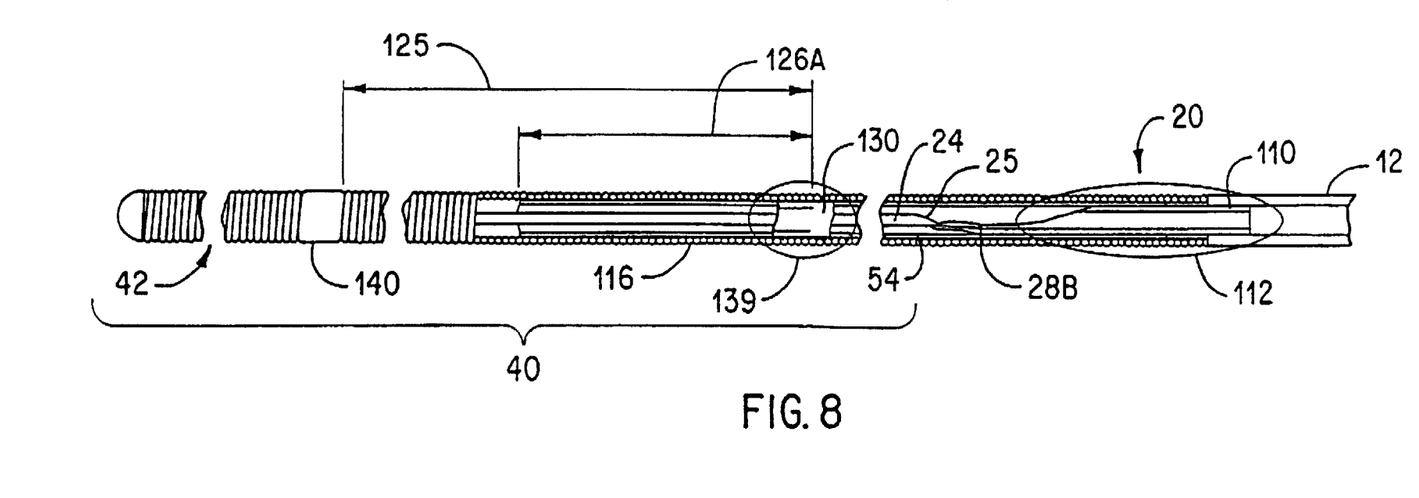
FIG. 8 is a partial cross sectional view of the transitional region and distal segment of a second alternative perfusion guidewire according to the invention.
Figure 10:
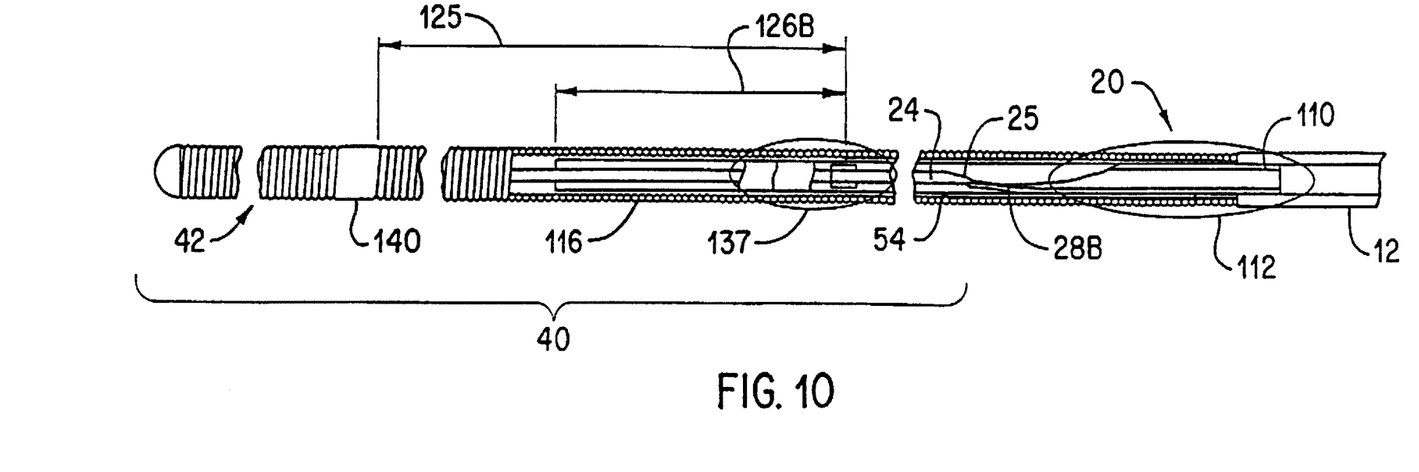
FIG. 10 is a partial cross sectional view of the transitional region and distal segment of a third alternative perfusion guidewire according to the invention.

As was discussed above with respect to FIGS. 3 and 4, transitional region 20 may include an elongated lip 28 or 28A which is formed from the distal end of tube 12. Alternatively, as is shown in FIGS. 6, 8, 10, and 12, a lip 28B may be formed from a separate tubular segment 110. By making lip 28B out of a separate tubular segment 110, the segment distal to lip 28B can be made with a substantially smaller outside diameter than would otherwise be possible if the lip were made from tube 12. Circled region 112 in FIGS. 6, 8, and 10 is shown enlarged in FIG. 12.

Figure 13:
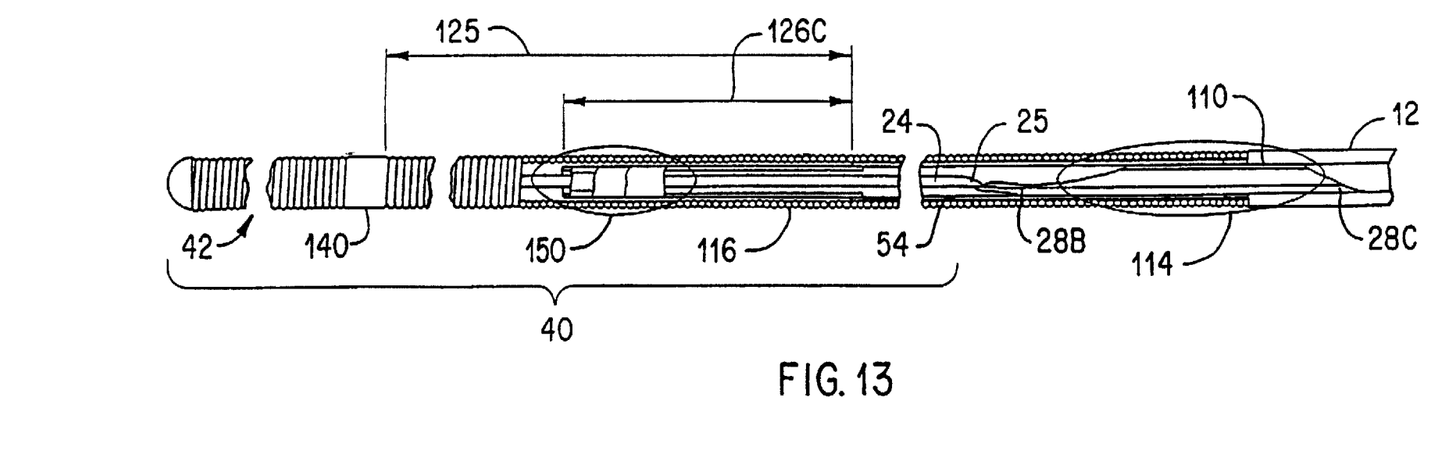
FIG. 13 is a partial cross sectional view of the transitional region and distal segment of a fourth alternative perfusion guidewire according to the invention.
Figure 14:
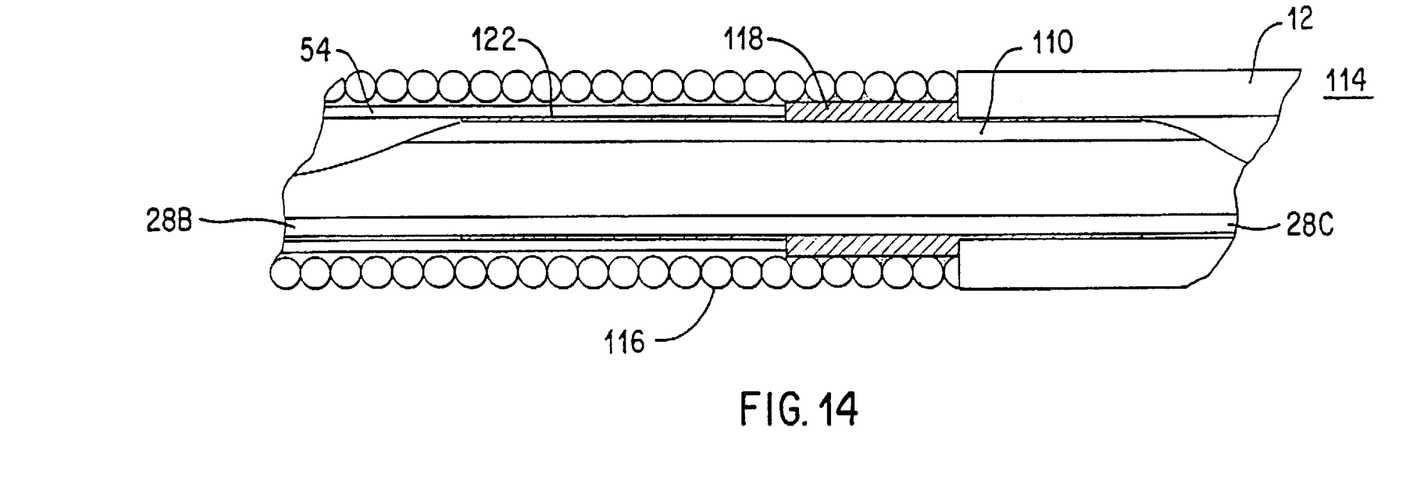
FIG. 14 is a partial cross sectional view of circled portion 114 of the distal segment shown in FIG. 13.

As is shown in FIGS. 13 and 14, tubular segment 110 may also include a second tapered lip 28C. Lip 28C provides a smooth transition from the larger inside diameter of tube 12 to the smaller inside diameter of tubular segment 110, and thus minimizes turbulence. Circled region 114 of FIG. 13 is shown enlarged as FIG. 14.

In cases where lip 28B or 28C must encounter vascular tortuosity, one or both may be fashioned into a helical form, as was discussed above with respect to FIG. 4. Lips 28B and 28C provide the same advantages as discussed above with respect to lips 28 and 28A.

Tubular segment 110 is preferably a 304 stainless steel tube having an inside diameter of 0.005", an outside diameter of 0.0075", and a length of 5 cm. Lips 28B (and where applicable 28C), are preferably approximately 1 cm long, and are preferably tapered smoothly to a final dimension of 0.006" wide by 0.001" thick.

In the embodiments shown in FIGS. 6, 8, 10, 12, 13, and 14, tubular segment 110 is typically joined to tube 12 and to stainless steel coil 116 with a lap joint 118 of an appropriate solder. Tubular segment 110 is also sealed with an overcladding or sheath of polyimide tubing 54. Polyimide tubing 54 is in turn surrounded by stainless steel coil 116, which preferably has an inside diameter of 0.010" and an outside diameter of 0.014". Polyimide tubing 54 can be sealed to tubular segment 110 via a leak tight lap bond 122 made of epoxy.

As in the above described embodiments, a core wire 24 is bonded to the distal end of lip 28B. Specifically, entrance taper 25 is preferably lap-joined with an appropriate solder to the distal end of lip 28B with an overlap of approximately 1.5 mm. Again, core wire 24 may be coated with a thin film of an appropriate hydrophilic coating.

Distal Segment

In the embodiments shown in FIGS. 6, 8, 10, and 13, distal segment 40 (i.e., the segment distal to lip 28B) generally includes core wire 24, a nonporous entrance region including tubing 54 and coil 116, a porous perfusion zone 125 including a baffle 126, and a standard floppy tip distal coil 42. Distal coil 42 is preferably separated from coil 116 by a solid solder joint 140. Baffle 126 provides a gradual pressure and flow velocity drop for high pressure fluids being perfused.

Fluid flows from transitional region 20 through tubing 54 (and around core wire 24) to baffle 126 in perfusion zone 125. Coil 116, which surrounds and supports tubing 54 and baffle 126 allows tubing 54 and baffle 126 to withstand high hydrostatic pressures.

The perfusion zone 125 is a porous region, typically about 6 cm long, through which the perfusion fluid is delivered. To effect "weeping" or low velocity flow, perfusion zone 125 includes porous baffle 126 surrounded by stainless steel coil 116. In general, porous baffle 126 can be any suitable structure which causes a pressure (and flow velocity) drop as the fluid exits to convert high pressure fluid flow (typically at least about 250 psi) to a low velocity, or "weeping" flow.

Baffle 126 preferably provides a flow velocity drop of at least one order of magnitude. The output of a low velocity, or "weeping" flow (as opposed to a flow including high velocity jets) from baffle 126 is atraumatic in that it reduces the possibility that fluid delivered by the guidewire will damage nearby tissue. A low velocity, or "weeping" flow from baffle 126 also reduces the possibility that cavitation or bubble formation will occur in the delivered fluid. As an example, at an ambient pressure of about 14.7 psi, an average blood pressure would be approximately 18 psi. Atraumatic pressure would be in this general range, but high enough to create flow. Preferably, for most applications where a pressure (and velocity) drop is required, the exit pressure will be less than about 25 psi, and the exit velocity will be less than about 200 cm/sec.

Such a pressure drop can be an important factor when high pressures are utilized with oxygen supersaturated perfusion treatments in order to maintain the oxygen partial pressure at sufficient levels downstream of a vessel-occluding procedure, such as balloon angioplasty. For example, in the delivery of oxygen supersaturated fluid according to the copending applications incorporated by reference herein, utilizing the present invention, it could be necessary to apply pressures in excess of about 1000 psi (and potentially 10,000 to 15,000 psi or higher) to ensure sufficient fluid flow and adequate oxygenation. As an example, a flow of about 35 ml per minute with perfusion of a supersaturated fluid as described in the above referenced applications can provide approximately 2 cc of oxygen per minute downstream of the treatment site in order to ensure a tissue oxygen partial pressure near acceptable levels (sustainable vessel blood flow rates typically are about 25 to 35 ml per minute in the large coronary arteries). Depending on the particular application, flow rates may be as low as about 1 ml per minute. For coronary applications, flow rates between about 10 and 50 ml per minute may be used and more specifically approximately 25 to 35 ml per minute. Oxygen can thus be delivered at rates between about 2 to 10 cc per minute and typically at least about 0.6 cc per minute. Utilizing the present invention with oxygen supersaturated fluids as described above can provide an oxygen partial pressure downstream of an occluding treatment site of at least about 75 mmHg and typically not less than about 100 mmHg. Preferable oxygen partial pressures of 1000 mmHg or greater may be achieved. Because of the high pressures that may be necessary to maintain adequate oxygen supply, the components of the invention preferably have a burst strength of at least about 1000 psi or higher to match the anticipated maximum pressures.

As shown in FIG. 6, for example, porous baffle 126 is sealed to polyimide tube 54 so that no flow can bypass porous baffle 126. Porous baffle 126 may be open or closed-ended, and preferably has length of at least approximately 2 cm. However, the length of baffle 126 may be tailored to suit the intended application, and it may be shorter than perfusion zone 125. Baffle 126 may include a polyimide tube having a plurality of fluid exit ports, one or more layers of porous polycarbonate or polyester tubing, or a combination of polyimide and polycarbonate (or polyester) tubing within coil 116. These combinations will be discussed further below.

Figure 9:
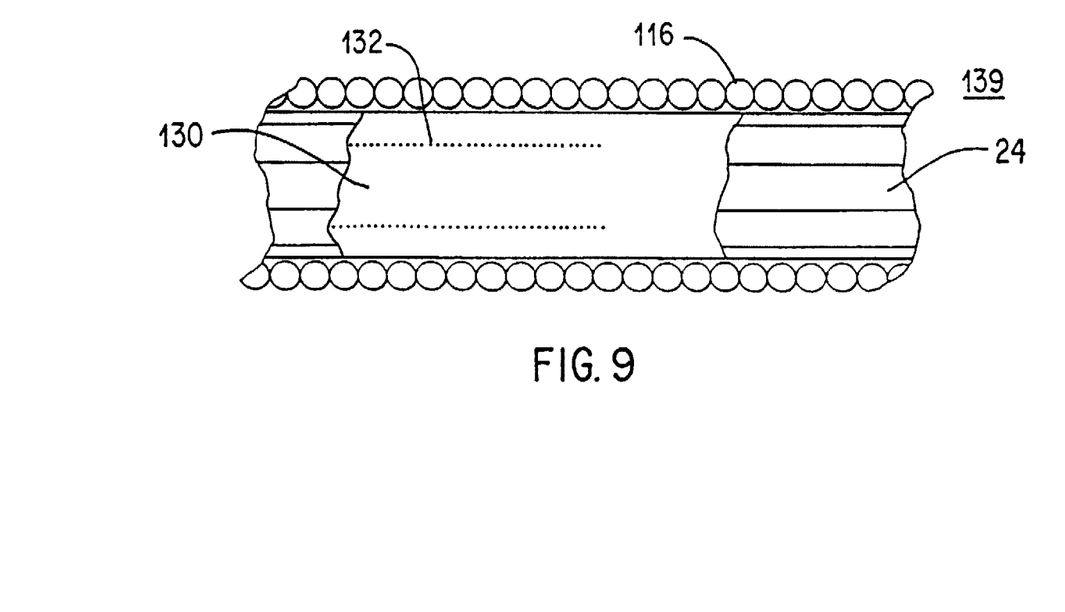
FIG. 9 is a partial cross sectional view of circled portion 139 of the distal segment shown in FIG. 8.

FIGS. 8 and 9 show a baffle 126A including a perforated polyimide tube 130. FIG. 9 is an enlarged view of the circled region 139 shown in FIG. 8. Tube 130 is perforated with a plurality of exit ports 132. Exit ports 132 may be formed with a laser, and are preferably each between 15–50 μm in diameter. Polyimide tubing 130 is surrounded by coil 116, which supports polyimide tube 130 and allows it to withstand high hydrostatic pressure. Polyimide tubing 130 may be bonded to polyimide tubing 54, or polyimide tubing 130 may be a continuous part of tubing 54. In one embodiment, the pressure of fluid exiting ports 132 causes the individual windings of coil 116 to spread apart, so that fluid may be delivered to a desired region. Alternatively, the windings of coil 116 may be pre-tensioned, during the fabrication stage, to provide a fixed spacing between the windings of between 10 and 60 microns.

Figure 11:
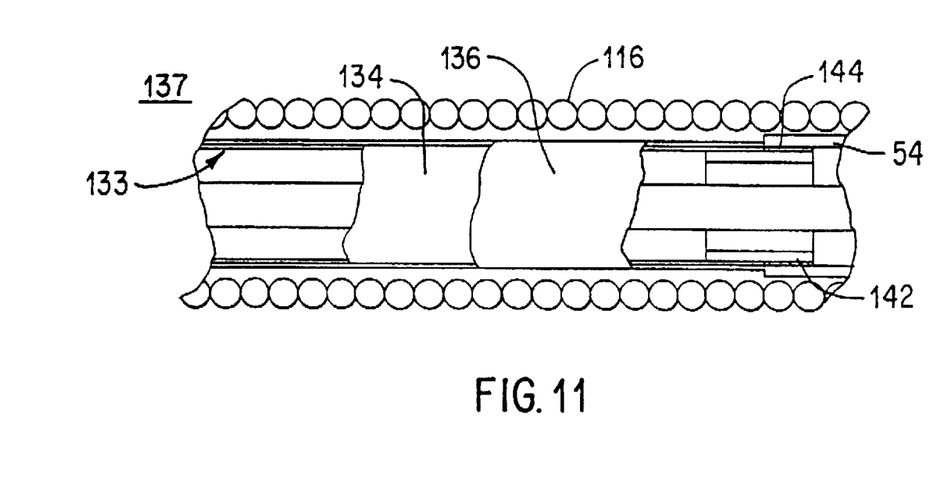
FIG. 11 is a partial cross sectional view of circled portion 137 of the distal segment shown in FIG. 10.
Figure 12:
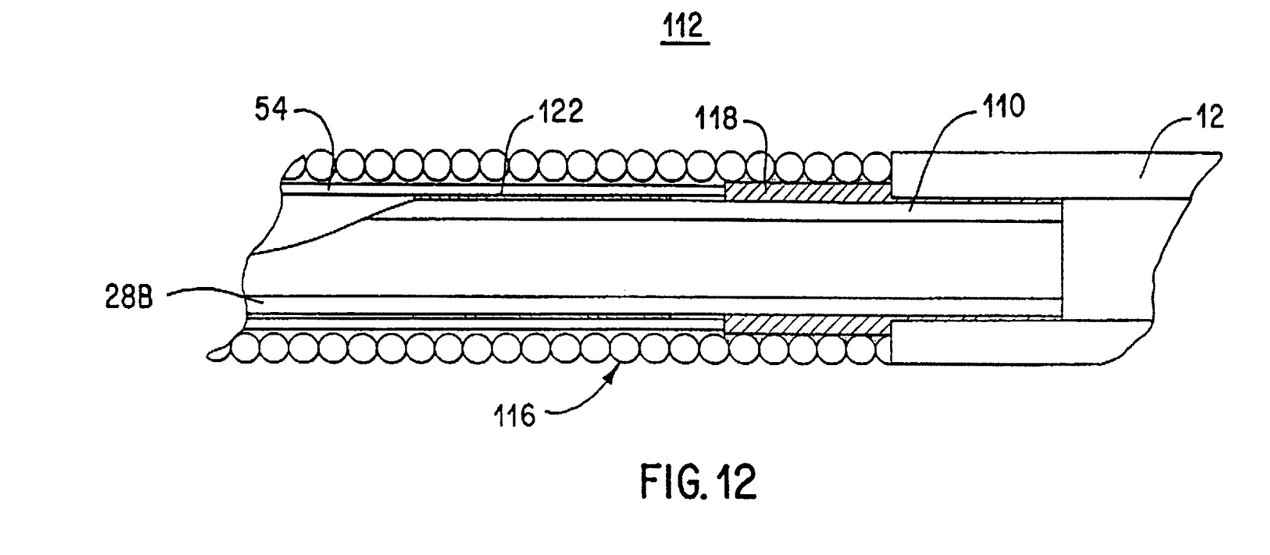
FIG. 12 is a partial cross sectional view of circled portion 112 of the transitional region shown in FIGS. 6, 8, and 10.

Referring now to FIGS. 10 and 11, a perfusion guidewire including a baffle 126B is shown. FIG. 11 is an enlarged view of the circled region 137 shown in FIG. 10. In baffle 126B, polyimide tube 54 is bonded, preferably with epoxy, to a rolled porous membrane, sheet, or tube 133 having a first ply 134 and a second ply 136. A short tubular member 142 (preferably made of polyimide) may also be used to bond polyimide tube 54 to rolled porous membrane 133. Porous membrane 133 may be any appropriate permeable material, including polyester and polycarbonate, or could be a screen or mesh of any appropriate material. A layer of epoxy 144 can be used to bond porous membrane 133 and polyimide tube 54 to tubular member 142. Plies 134 and 136 preferably have a 3 to 5 micron porosity, and are each about 6 microns thick. A single ply of porous material could also be used if desired. Additional plies of porous material will have the effect of further reducing the velocity of the delivered perfusion fluid.

Again, fluid flows out from plies 134 and 136 and then passes through the windings of stainless steel coil 116. The coils of stainless steel coil 116 may be spread apart by the hydrostatic pressure exerted by the fluid flowing from the porous membrane 133, or the windings of coil 116 may be pre-tensioned, during the fabrication stage, to provide a fixed spacing between the windings of between 10 and 60 microns.

Figure 7:
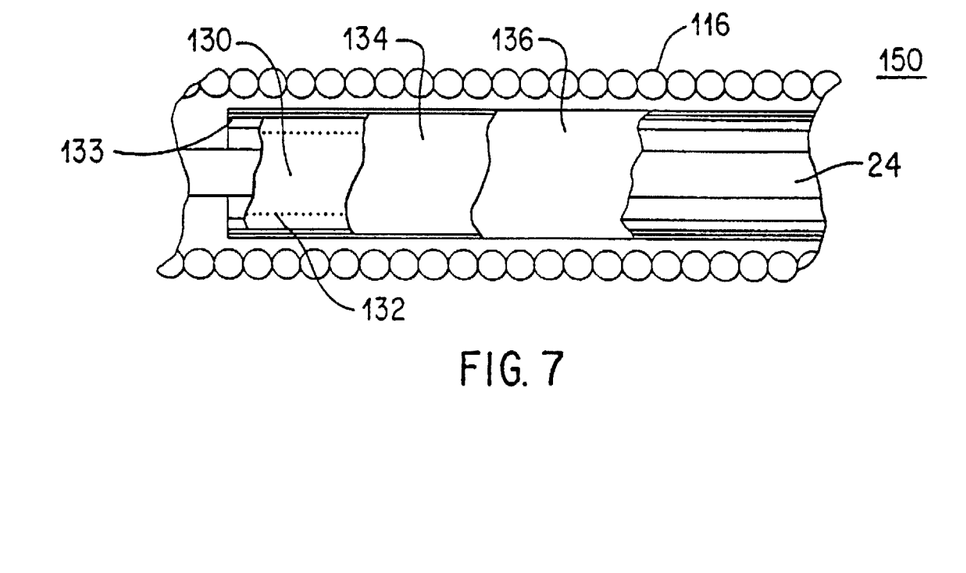
FIG. 7 is a partial cross sectional view of circled portion 150 of the distal segment shown in FIGS. 6 and 13.

Referring now to FIGS. 6, 7, and 13, a perfusion guidewire including a baffle 126C is shown. FIG. 7 is an enlarged view of circled region 150 shown in FIGS. 6 and 13. Baffle 126C preferably includes a first layer of perforated polyimide tubing 130 (including a plurality of exit ports 132) and a rolled porous membrane, tube, or sheet 133, having a first ply 134 and a second ply 136. As was discussed above with respect to the other embodiments, polyimide tubing 54 may be bonded to tubing 130 and porous membrane 133 using epoxy alone, or epoxy in combination with a separate tubular member. Tubing 130 may also form a part of tubing 54. The combination of the polyimide tube 130 with the porous membrane 133 within coil 116 reduces the possibility that high velocity jets of liquid will exit coil 116 during a perfusion procedure. Again, this ensures a low velocity, "weeping", atraumatic flow which minimizes the possibility of cavitation or bubble formation during the delivery of the oxygen supersaturated fluid, and which will minimize the possibility of damaging, or causing trauma to nearby body tissues.

Figure 15:
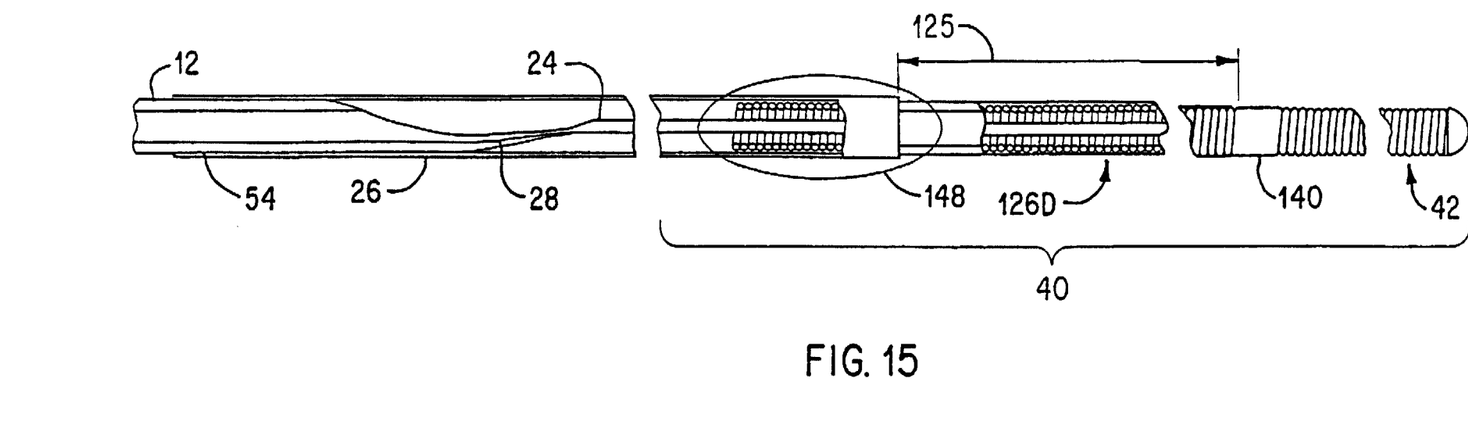
FIG. 15 is a partially cross sectional view of the transitional region and distal segment of a fifth alternative perfusion guidewire according to the invention.
Figure 16:
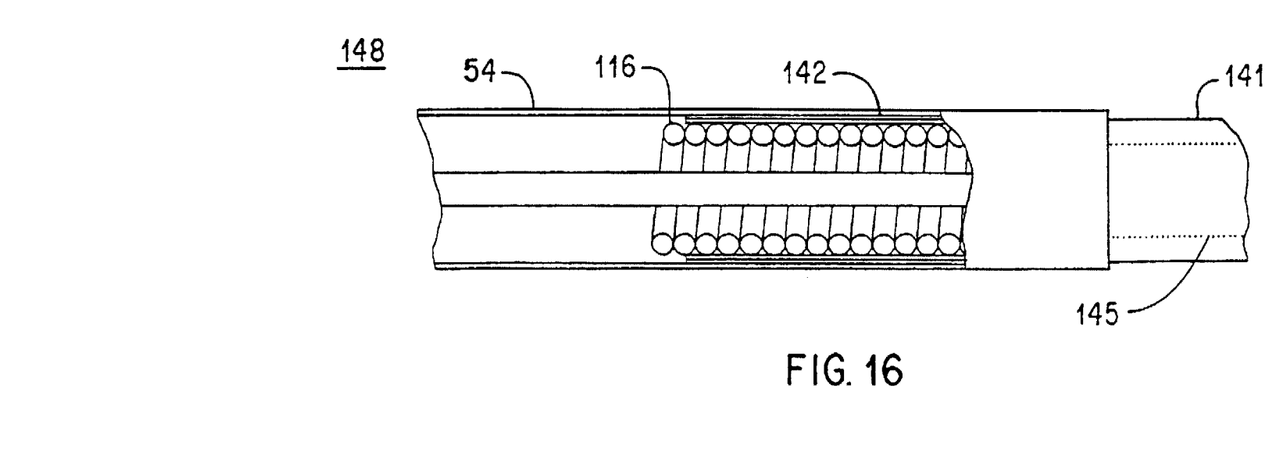
FIG. 16 is a partial cross sectional view of circled portion 148 of the transitional region shown in FIG. 15.

Referring now to FIGS. 15 and 16, an alternative embodiment of a perfusion guidewire is shown. FIG. 16 is an enlarged view of circled region 148 in FIG. 15. In FIGS. 15 and 16, polyimide tube 54 is bonded to tube 141 with a layer of epoxy 142. Tube 141 may be made of polyester heat shrink tubing, polyimide tubing, or any other suitable material. Tube 141 has a plurality of perforations 145. Thus, baffle 126D of perfusion region 125 is formed by tube 141 which fits over coil 116. In operation, fluid flows out of the windings of coil 116, and then out of perforations 145. Again, windings of coil 116 may be forced apart by the hydrostatic pressure of the fluid being delivered, or the windings of coil 116 may be pre-tensioned during the fabrication stage.

The present invention has been described in terms of a preferred embodiment. The invention, however, is not limited to the embodiment depicted and described. Rather, the scope of the invention is defined by the appended claims.

What is claimed is:

1. A perfusion guidewire for the delivery of liquid, comprising:
   a tubular housing defining a fluid lumen therethrough, the housing having a proximal end and a distal end, wherein the distal end of the housing is formed in the shape of an elongated tapered lip;
   a core wire having a proximal end and a distal end, the proximal end of the core wire being secured to the tapered lip of the tubular housing;
   a first coil mounted at the distal end of the core wire; and
   an elongated cylindrical sheath extending from an area proximal to the tapered lip and over a portion of the core wire, the sheath defining a continuation of the fluid lumen and having at least one fluid exit.

2. A guidewire as in claim 1, wherein the tubular housing is an elongated, flexible member having a cylindrical side wall, a portion of the side wall being removed such that a remaining portion of the side wall forms said elongated tapered lip.

3. A guidewire as in claim 2, wherein the elongated tapered lip forms an open helix which reduces cast in the guide wire.

4. A guidewire as in claim 1, further comprising a coil surrounding at least a portion of the cylindrical sheath.

5. A guidewire as in claim 4, wherein the first coil and the coil surrounding at least a portion of the cylindrical sheath comprise a single coil extending from the tubular housing to the guidewire distal end.

6. A guidewire as in claim 1 wherein the elongated tapered lip is helical.

7. A guidewire as in claim 1 wherein the elongated cylindrical sheath is made of polymer tubing.

8. A guidewire as in claim 7 wherein the distal end of the polymer tubing is open.

9. A guidewire as in claim 7 wherein the distal end of the polymer tubing is sealed.

10. A guidewire as in claim 9 wherein the polymer tubing has a plurality of perforations.

11. A guidewire as in claim 10 further including a second, elongated coil mounted over the polymer tubing.

12. A guidewire as in claim 11 further including a porous membrane mounted between the polymer tubing and the second coil.

13. A guidewire as in claim 10 further including a second, elongated coil mounted underneath the polymer tubing.

14. A guidewire as in claim 1, wherein the elongated tapered lip comprises an elongated member secured to the distal end of the tubular housing.

15. A perfusion guidewire suitable for the delivery of oxygen supersaturated liquid, comprising:
   a high pressure tubular housing defining a lumen therein, the high pressure tubular housing having a proximal end and a distal end;
   a tubular segment mounted within the distal end of the high pressure tubular housing, the tubular segment having a proximal end and a distal end;
   the distal end of the tubular segment formed in the shape of an elongated tapered lip;

a core wire having a proximal end and a distal end;

the proximal end of the core wire being tapered and bonded to the tapered lip;

a first coil mounted on the distal end of the core wire;

an elongated cylindrical sheath extending from at least an area proximal to the tapered lip, and extending over a substantial portion of the core wire;

the elongated cylindrical sheath having at least one fluid exit; and a second, elongated coil mounted over the elongated cylindrical sheath.

16. A perfusion guidewire as in claim 15 wherein the elongated cylindrical sheath includes a non-porous section immediately distal to the tubular housing, and a porous section distal to the non-porous section.

17. A perfusion guidewire as in claim 16 wherein the porous section of the elongated cylindrical sheath includes perforated tubing.

18. A perfusion guidewire as in claim 17 wherein the porous section of the elongated cylindrical sheath includes perforated tubing surrounded by a permeable membrane.

19. A perfusion guidewire as in claim 16 wherein the porous section of the elongated cylindrical tubing includes a permeable membrane.

20. A high pressure perfusion guidewire as in claim 15 wherein the proximal end of the tubular segment is also formed in the shape of an elongated tapered lip.

21. A high pressure perfusion guidewire as in claim 15 wherein the distal end of the elongated cylindrical sheath is open.

22. A high pressure perfusion guidewire as in claim 15 wherein the distal end of the elongated cylindrical sheath is closed.

23. A perfusion guidewire suitable for replacement of standard guidewires and for the delivery of fluid to a treatment site, comprising:

a tubular housing defining a fluid lumen therethrough, the housing having a proximal end and a distal end;

a core wire disposed at the distal end of the tubular housing and having a proximal end and a distal end;

wherein the distal end of the tubular housing and the proximal end of the core wire comprise a transition zone that provides a smooth transition in flexibility and uniform transmission of torque as between the tubular housing and core wire such that the guidewire exhibits handling characteristics substantially the same as standard guidewires;

a first coil mounted at the distal end of the core wire; and an elongated cylindrical sheath extending from the tubular housing and over a portion of the core wire, the sheath defining a continuation of the fluid lumen and having at least one fluid exit.

24. The guidewire according to claim 23, wherein the transition zone includes means for joining the tubular housing and core wire, the tubular housing being provided with a gradually increasing flexibility in the direction of the distal end.

25. The guidewire according to claim 24, wherein a tapered lip is formed at the distal end of the tubular housing, and the proximal end of the core wire is secured to said tapered lip.

26. The guidewire according to claim 25, wherein the tubular housing is an elongated, flexible member having a cylindrical side wall, a portion of the tubular housing side wall being removed such that a remaining portion of the side wall forms said tapered lip.

27. A perfusion guidewire, comprising:

a flexible, torque transmitting, high pressure tubing defining a fluid lumen therethrough, the tubing having a proximal end and a distal end;

a core wire having a proximal end and a distal end, the proximal end of the core wire being disposed at the distal end of the tubing;

a first coil mounted at the distal end of the core wire;

an elongated cylindrical sheath extending from the tubular housing over a portion of the core wire, the sheath defining a continuation of the fluid lumen; and a baffle zone extending along at least a portion of the core wire, the baffle zone defining at least one fluid exit and including perforated tubing surrounded by a permeable membrane, the permeable membrane surrounded by a second, elongated coil, wherein the baffle zone creates a flow velocity drop such that fluid perfused through said guidewire leaves said fluid exit under atraumatic conditions.

28. The guidewire according to claim 27, wherein the high pressure tubing has a burst strength exceeding about 1000 psi.

29. The guidewire according to claim 27, wherein the baffle zone provides a flow velocity drop of at least one order of magnitude.

30. The guidewire according to claim 27, wherein the baffle zone provides an atraumatic fluid exit velocity of less than about 200 cm/sec.

31. A perfusion guidewire, comprising:

a flexible, torque transmitting, high pressure tubing defining a fluid lumen therethrough, the tubing having a proximal end and a distal end;

a core wire having a proximal end and a distal end;

a transition zone that joins the distal end of the high pressure tubing to the proximal end of the core wire to provide a smooth transition in flexibility and uniform transmission of torque as between said tubing and core wire, the transition zone including means for joining the high pressure tubing and core wire such that the tubing is provided with a gradually increasing flexibility in the direction of the distal end;

a first coil mounted at the distal end of the core wire;

an elongated cylindrical sheath extending from the tubular housing over a portion of the core wire, the sheath defining a continuation of the fluid lumen; and a baffle zone extending along at least a portion of the core wire, the baffle zone defining at least one fluid exit and comprising means for creating a flow velocity drop such that fluid perfused through said guidewire leaves said fluid exit under atraumatic conditions.

32. The guidewire according to claim 31, wherein the distal end of the tubing is formed in the shape of an elongated tapered lip.

* * * * *